(12) United States Patent
Wu et al.

(10) Patent No.: US 11,135,259 B2
(45) Date of Patent: Oct. 5, 2021

(54) COMPOSITIONS AND METHODS FOR INCREASING NITRIC OXIDE LEVELS FOR MALE PERFORMANCE

(71) Applicant: WORLD PHARMACEUTICAL TECHNOLOGY, LLC., Rowland Heights, CA (US)

(72) Inventors: Yong Wu, Downey, CA (US); Ke Wu, Wuhan (CN); Gordon Lee, Rowland Heights, CA (US); Wei Cao, Downey, CA (US); Huabing Yang, Wuhan (CN)

(73) Assignee: WORLD PHARMACEUTICAL TECHNOLOGY, LLC, Rowland Heights, CA (US)

(*) Notice: Subject to any disclaimer, the term of this patent is extended or adjusted under 35 U.S.C. 154(b) by 14 days.

(21) Appl. No.: 16/239,475

(22) Filed: Jan. 3, 2019

(65) Prior Publication Data

US 2019/0365842 A1  Dec. 5, 2019

Related U.S. Application Data

(60) Provisional application No. 62/677,654, filed on May 29, 2018.

(51) Int. Cl.

| | | |
|---|---|---|
| *A61K 36/296* | (2006.01) | |
| *A61K 36/63* | (2006.01) | |
| *A61P 15/10* | (2006.01) | |
| *A61K 36/88* | (2006.01) | |
| *A61K 31/133* | (2006.01) | |
| *A61K 31/4406* | (2006.01) | |
| *A61K 36/185* | (2006.01) | |
| *A61K 31/385* | (2006.01) | |
| *A61K 36/258* | (2006.01) | |
| *A61K 36/889* | (2006.01) | |
| *A61K 33/06* | (2006.01) | |
| *A61K 33/30* | (2006.01) | |
| *A61K 36/31* | (2006.01) | |
| *A61K 36/899* | (2006.01) | |
| *A61K 31/185* | (2006.01) | |
| *A61K 31/198* | (2006.01) | |
| *A61K 31/352* | (2006.01) | |

(52) U.S. Cl.
CPC ............ *A61K 36/63* (2013.01); *A61K 31/133* (2013.01); *A61K 31/185* (2013.01); *A61K 31/198* (2013.01); *A61K 31/352* (2013.01); *A61K 31/385* (2013.01); *A61K 31/4406* (2013.01); *A61K 33/06* (2013.01); *A61K 33/30* (2013.01); *A61K 36/185* (2013.01); *A61K 36/258* (2013.01); *A61K 36/296* (2013.01); *A61K 36/31* (2013.01); *A61K 36/88* (2013.01); *A61K 36/889* (2013.01); *A61K 36/899* (2013.01); *A61P 15/10* (2018.01)

(58) Field of Classification Search
None
See application file for complete search history.

*Primary Examiner* — Jessica Worsham
(74) *Attorney, Agent, or Firm* — Lewis Roca Rothgerber Christie LLP (57) ABSTRACT

Compositions for improving erectile function or treating erectile dysfunction include active ingredients of Muira Puama extract, Quercetin, *Chlorophytum borivilianum* (Safed Musli), Dimethylethanolamine (DMAE), niacin, *Tribulus terrestris* extract, alpha-lipoic acid, Horny Goat Weed (*Epimedium* grandfiflorum), *Panax ginseng*, and saw palmetto berry extract, and may also include magnesium aspartate, Zinc oxide, and Maca root (*Lepidium meyenii*). Additional active ingredients include *Avena sativa* extract (oat straw), L-Taurine, L-Lysine hydrochloride (HCl), a L-Arginine, and/or L-Carnitine.

20 Claims, 5 Drawing Sheets
(3 of 5 Drawing Sheet(s) Filed in Color)

COMPOSITIONS AND METHODS FOR INCREASING NITRIC OXIDE LEVELS FOR MALE PERFORMANCE

CROSS-REFERENCE TO RELATED APPLICATION(S)

The present application claims priority to and the benefit of U.S. Provisional Application Ser. No. 62/677,654 filed on May 29, 2018, entitled "Composition and Method of Increasing Nitric Oxide Levels for Male Performance," the entire content of which is incorporated herein by reference.

BACKGROUND

Figure 1:
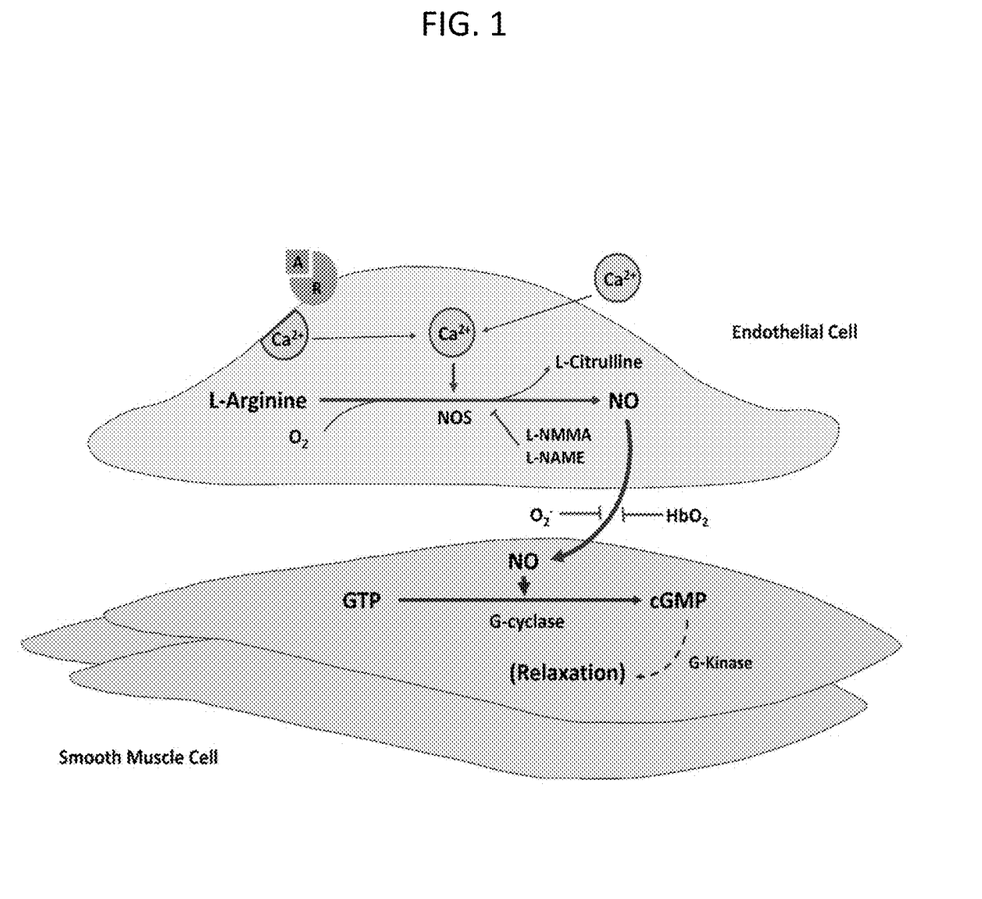
FIG. 1 is a schematic depicting the molecular mechanisms of cGMP-dependent relaxation of smooth muscle cells through endothelial cells in which an Agonist (A) (e.g., acetylcholine, bradykinin, or histamine) is shown binding to receptor (R) of an endothelial cell thereby activating $Ca^{2+}$ influx and increasing intracellular $Ca^{2+}$ with the increase in intracellular $Ca^{2+}$ in turn activating endothelial nitric oxide synthase (NOS) as well as an oxygenase to catalyze L-arginine and other co-substrates and co-factors to produce nitric oxide (NO) which diffuses out of the endothelial cell and into the smooth muscle cells (SMCs) where the NO activates G-cyclase catalysis of guanosine triphosphate (GTP) to cyclic guanosine monophosphate (cGMP) to induce relaxation of the smooth muscle.

Impotence or erectile dysfunction (ED) is a problem that most men will experience at some time in their life. Erectile dysfunction (ED) associated with the aging process is characterized histologically within the cavernosa by a progressive apoptosis or loss of the corporal smooth muscle cells (SMC) and replacement of these cells with collagen (this may be referred to as fibrosis), and smooth muscle (SM) relaxation is impaired. It has been estimated that once approximately 15-20% of the corporal SMCs have been lost, venous leakage or corporal veno-occlusive dysfunction (CVOD) becomes clinically apparent. It has been demonstrated that as these aging-related histological changes begin to occur in the cavernosa, the SMCs attempt to counter these apoptotic and fibrotic changes by upregulating inducible nitric oxide synthase (iNOS). The high output of nitric oxide (NO) produced intracellularly by iNOS can act as an anti-fibrotic factor. With reference to FIG. 1, NO produced in endothelial cells diffuses to smooth muscle cells (SMCs) where it activates guanylyl-cyclase, thereby effecting an increase in cyclic guanosine mono-phosphate (cGMP) which mediates smooth muscle cell relaxation. The cGMP-induced SM relaxation is mediated mainly by cGMP-dependent protein kinase activation. It involves several molecular events culminating in a reduction in intracellular calcium ($Ca^{2+}$) concentration and a decrease in the sensitivity of the contractile system to $Ca^{2+}$.

Despite the ongoing commercial success of prescription medications under the trademarks VIAGRA®(sildenafil), LEVITRA® (vadenafil) and CIALIS®. (tadafil) for treatment of ED, there remains a need to treat ED before it progresses to the point where pharmacological and/or other medical intervention is required in order to have desired sexual performance. Furthermore, current ED drugs, such as VIAGRA® and CIALIS® are generally prescribed only after the patient has presented with symptoms of ED.

SUMMARY

Aspects of embodiments of the present disclosure include compositions for improving erectile function or treating erectile dysfunction in a male subject (e.g., human) in need of improved erectile function or a male suffering from erectile dysfunction. Aspects of embodiments of the present disclosure include methods for improving erectile function or treating erectile dysfunction, the methods include administering one of the compositions of the present disclosure to a male subject in need of improved erectile function or a male suffering from erectile dysfunction.

In some embodiments of the present disclosure a composition for improving erectile function or treating erectile dysfunction in a male subject is a composition including Muira Puama extract, Quercetin, *Chlorophytum borivilianum* (Safed Musli), Dimethylethanolamine (DMAE), niacin (Vitamin B3), *Tribulus terrestris* extract, alpha-lipoic acid, Horny Goat Weed (*Epimedium grandfiflorum*), Korean ginseng (*Panax ginseng*), and saw palmetto berry extract. In some embodiments, the composition also includes magnesium aspartate, Zinc oxide, and/or Maca root (*Lepidium meyenii*). In some embodiments, the composition also includes one or more of *Avena sativa* extract (oat straw), L-Taurine, L-Lysine, L-Arginine, and/or L-Carnitine.

In some embodiments of the present disclosure, the composition as disclosed above includes the Muira Puama extract in an amount of about 15 mg to about 100 milligrams (mg), the Quercetin in an amount of about 10 mg to about 75 mg, *Chlorophytum borivilianum* in an amount of about 100 mg to about 600 mg, DMAE in an amount of about 20 mg to about 120 mg, niacin in an amount of about 3 mg to about 20 mg, *Tribulus terrestris* extract in an amount of about 20 mg to about 120 mg, alpha-lipoic acid in an amount of about 60 mg to about 400 mg, Horny Goat Weed (*Epimedium grandfiflorum*) in an amount of about 50 mg to about 300 mg, *Panax ginseng* in an amount of about 20 mg to about 120 mg, saw palmetto berry extract in an amount of about 10 mg to about 75 mg, magnesium aspartate is in an amount of about 5 mg to about 35 mg, Zinc oxide in an amount of about 3 mg to about 20 mg, and Maca root (*Lepidium meyenii*) in an amount of about 50 mg to about 300 mg.

In some embodiments of the present disclosure, the composition as disclosed above includes the *Avena sativa* extract (oat straw) in an amount of about 20 mg to about 120 mg, the L-Taurine in an amount of about 4 mg to about 25 mg, the L-Lysine in an amount of about 4 mg to about 25 mg, the L-Arginine in an amount of about 4 mg to about 25 mg, and/or the L-Carnitine in an amount of about 4 mg to about 25 mg.

In some embodiments of the present disclosure, the active ingredients of the composition as disclosed above are in a ratio of the Muira Puama extract at about 22.50 mg with the Quercetin at about 15 mg, the *Chlorophytum borivilianum* at about 125 mg, the DMAE at about 25 mg, the niacin at about 3.75 mg, the *Tribulus terrestris* Extract at about 25 mg, the alpha-lipoic acid at about 75 mg, the Horny Goat Weed (*Epimedium grandfiflorum*) at about 62.50 mg, the Korean ginseng (*Panax ginseng*) at about 25 mg, and the saw palmetto berry extract at about 15 mg.

In some embodiments of the present disclosure, the active ingredients of the composition are disclosed above and are in a ratio of the Muira Puama extract at about 22.50 mg with the Quercetin at about 15 mg, the *Chlorophytum borivilianum* at about 125 mg, the DMAE at about 25 mg, the niacin at about 3.75 mg, the *Tribulus terrestris* Extract at about 25 mg, the alpha-lipoic acid at about 75 mg, the Horny Goat Weed (*Epimedium grandfiflorum*) at about 62.50 mg, the *Panax ginseng* at about 25 mg, the saw palmetto berry extract at about 15 mg, the magnesium aspartate at about 7.50 mg, the Zinc oxide at about 3.5 mg, and the Maca root (*Lepidium meyenii*) at about 62.50 mg.

In some embodiments of the present disclosure, the active ingredients of the composition are disclosed above and are in a ratio of the Muira Puama extract at about 22.50 mg with the Quercetin at about 15 mg, the *Chlorophytum borivilianum* at about 125 mg, the DMAE at about 25 mg, the niacin at about 3.75 mg, the *Tribulus terrestris* Extract at about 25 mg, the alpha-lipoic acid at about 75 mg, the Horny Goat Weed (*Epimedium grandfiflorum*) at about 62.50 mg, the *Panax ginseng* at about 25 mg, the saw palmetto berry extract at about 15 mg, the magnesium aspartate at about 7.50 mg, the Zinc oxide at about 3.5 mg, the Maca root (*Lepidium meyenii*) at about 62.50 mg, the *Avena sativa* extract at about 25 mg, the L-Taurine at about 5 mg, the L-Lysine at about 5 mg, the L-Arginine at about 5 mg, and the L-Carnitine at about 5 mg.

In some embodiments of the present disclosure, the active ingredients of the composition includes the Muira Puama extract in an amount of about 22.50 mg, the Quercetin in an amount of about 15 mg, the *Chlorophytum borivilianum* in an amount of about 125 mg, the DMAE in an amount of about 25 mg, the niacin in an amount of about 75 mg, the Horny Goat Weed (*Epimedium grandfiflorum*) in an amount of about 62.50 mg, the *Panax ginseng* in an amount of about 25 mg, the saw palmetto berry extract in an amount of about 15 mg, the magnesium aspartate in an amount of about 7.50 mg, the Zinc oxide in an amount of about 3.5 mg, the Maca root (*Lepidium meyenii*) in an amount of about 62.50 mg, the *Avena sativa* extract in an amount of about 25 mg, the L-Taurine in an amount of about 5 mg, the L-Lysine in an amount of about 5 mg, the L-Arginine in an amount of about 5 mg, and the L-Carnitine in an amount of about 5 mg.

In some embodiments of the present disclosure, the composition as disclosed above and herein is a solid oral composition or a liquid oral composition. For example, the solid oral composition may be a tablet or a capsule.

In some embodiments of the present disclosure, the composition as disclosed above and herein also includes an excipient. Non-limiting examples of an excipient include cellulose, rice flour, magnesium stearate, gelatin, and/or a colourant.

In some embodiments of the present disclosure, a method for improving erectile function or decreasing erectile dysfunction in a male subject, includes administering any one of the compositions of the present disclosure to the male subject.

In some embodiments of the present disclosure, the composition of the present disclosure is in tablet or capsule form and a method for improving erectile function or decreasing erectile dysfunction in a male subject, includes administering 4 tablets or capsules per day to the male subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, together with the specification, illustrate example embodiments of the present disclosure, and, together with the description, serve to explain principles of the present disclosure.

These and other features and advantages of embodiments of the present disclosure will become more apparent by reference to the following detailed description when considered in conjunction with the following drawings.

DETAILED DESCRIPTION

Aspects of embodiments of the present disclosure include compositions and methods for stimulating the libido and improving overall sexual health in men. In particular, compositions and methods of the present disclosure improve erectile function and/or alleviate or postpone the progression of erectile dysfunction in men. The compositions include all natural ingredients including herbs or herbal extracts.

The effectiveness and safety (e.g., nontoxicity) of the compositions of the present disclosure are the result of the specific mixture of the all-natural components. The specific ratios of the components in the compositions allow for the use of less of the more toxic components which have significant efficacy on improving sexual health of men.

As used herein, the terms "XL-1" and "XtraLast" are used interchangeably to refer to a composition according to embodiments of the present disclosure that includes a formulation for oral administration made of any combination of components (e.g., active ingredients) as disclosed herein.

As used herein, the term "component" refers to each active ingredient (AI) in any of the combinations as disclosed herein for the XL-1 composition. The list of possible components for the XL-1 composition is listed in Table 1 as ACTIVE INGREDIENTS. The possible components for the XL-1 composition include Muira Puama extract, Quercetin, *Chlorophytum borivilianum* (Safed Musli), Dimethylethanolamine (DMAE or DMEA), Vitamin B3 (niacin), *Tribulus terrestris* extract, alpha-lipoic acid, Horny Goat Weed (*Epimedium grandfiflorum*), *Panax ginseng* (Korean *ginseng*), saw palmetto berry extract, magnesium aspartate, zinc oxide, Maca root (*Lepidium meyenii*), *Avena sativa* extract (oat straw), L-Taurine, L-Lysine hydrochloride (HCl), L-Arginine and/or L-Carnitine. The amounts and ranges as well as ratios disclosed herein for each component are based on specifications for each component as disclosed herein. For any component specifications that are not disclosed, the component formulation is a standard formulation.

As used herein, the term "standardized extract" refers to a powdered or liquid extract prepared with a measured (e.g., standardized) amount (e.g., a percentage) of a major active ingredient or major active ingredients within the herb such that the active ingredients are equal throughout the extract.

As used herein, the term "ratio extract" a fluid extract or a solid extract which is prepared by evaporation methods to removal all liquids and the ratio refers to the number of herb plants to create one part extract. For example, an extract having a ratio of 4:1 was made with 4 herb plants to make 1 part extract.

As used herein, the term "powder" or "powder extract" refers to a powdered version of a fluid extract or solid extract, in which the powder is made by evaporation methods to remove all liquids. Powder extracts have a concentration ratio of 1:1 or higher.

As used herein, Muira Puama extract is a 4:1 ratio extract.

As used herein, Quercetin is at 95% concentration.

As used herein, *Chlorophytum borivilianum* (Safed Musli) is a standardized extract having 50% saponins.

As used herein, *Tribulus terrestris* extract is a standardized extract at 90%.

As used herein, Horny Goat Weed is a standardized extract at 10%.

As used herein, *Panax ginseng* (Korean *ginseng*) is a standardized extract at 5%.

As used herein, magnesium is magnesium aspartate.

As used herein, zinc is zinc oxide.

As used herein, Maca root (*Lepidium meyenii*) (or tubers) is a standardized extract powder at 0.6%.

As used herein, *Avena sativa* extract (oat straw) is a 10:1 ratio extract.

As used herein, "L-Lysine," "L-Lysine hydrochloride," and "L-Lysine HCl" are used interchangeably to refer to the L-Lysine component of the XL-1 composition which is in the form of the hydrochloride salt of L-Lysine.

As used herein, an "excipient" refers to any ingredient other than the disclosed "components" or "active ingredients" of the XL-1 composition. The XL-1 composition of the present disclosure may be administered alone without any excipients. However, in some embodiments, the XL-1 composition may be administered as a formulation in association with one or more acceptable excipients.

XL-1 compositions of the present disclosure may be administered orally in the form a tablet or a capsule. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids or powders, lozenges (including liquid-filled), chews, multi- and nano-particulates, gels, films (including muco-adhesive), ovules, sprays and liquid formulations.

XL-1 compositions for use according to the present disclosure may also be used in fast-dissolving, fast disintegrating dosage forms such as those described in Expert Opinion in Therapeutic Patents, 11(6), 981-986 by Liang and Chen (2001), the entire content of which is incorporated herein by reference.

A tablet form of the XL-1 composition may be prepared using standard processes known to a formulation chemist, for example, by direct compression, granulation (dry, wet or melt), melt congealing, or extrusion. The tablet formulation may comprise one or more layers and may be coated or uncoated.

Examples of excipients suitable for oral administration include carriers, for example, cellulose (e.g., microcrystalline cellulose), rice flour, calcium carbonate, dibasic calcium phosphate, mannitol and sodium citrate, granulation binders, for example, polyvinylpyrrolidine, hydroxypropylcellulose (HPC), hydroxypropylmethylcellulose (HPMC) and gelatin, disintegrants, for example, sodium starch glycollate and silicates, lubricating agents, for example, magnesium stearate and stearic acid, wetting agents, for example, sodium lauryl sulphate, preservatives, anti-oxidants, flavours and colourants. For example, any color additive may be included, e.g., FD&C (Food, Drugs, and Cosmetics) Blue No. 1.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are disclosed in Verma et al, Pharmaceutical Technology On-line, 25(2), 1-14 (2001), the entire content of which is incorporated herein by reference. Other modified release formulations are described in U.S. Pat. No. 6,106,864, the entire content of which is incorporated herein by reference.

In some embodiments of the present disclosure, the XL-1 composition is made of at least Muira Puama extract, Quercetin, *Chlorophytum borivilianum* (Safed Musli), Dimethylethanolamine (DMAE or DMEA), Vitamin B3 (niacin), *Tribulus terrestris* Extract, alpha-lipoic acid, Horny Goat Weed (*Epimedium grandfiflorum*), Korean *ginseng* (*Panax ginseng*), and saw palmetto berry extract.

In some embodiments of the present disclosure, the tablet or capsule of the XL-1 composition includes Muira Puama extract in an amount of about 15 mg to about 100 milligrams (mg), Quercetin in an amount of about 10 mg to about 75 mg, *Chlorophytum borivilianum* in an amount of about 100 mg to about 600 mg, dimethylethanolamine (DMAE or DMEA) in an amount of about 20 mg to about 120 mg, Vitamin B3 (niacin) in an amount of about 3 mg to about 20 mg, *Tribulus terrestris* Extract in an amount of about 20 mg to about 120 mg, alpha-lipoic acid in an amount of about 60 mg to about 400 mg, Horny Goat Weed (*Epimedium grandfiflorum*) in an amount of about 50 mg to about 300 mg, Korean *ginseng* (*Panax ginseng*) in an amount of about 20 mg to about 120 mg, and saw palmetto berry extract in an amount of about 10 mg to about 75 mg.

In some embodiments of the present disclosure, the tablet or capsule of the XL-1 composition includes at least Muira Puama extract, Quercetin, *Chlorophytum borivilianum* (Safed Musli), Dimethylethanolamine (DMAE or DMEA), Vitamin B3 (niacin), *Tribulus terrestris* Extract, alpha-lipoic acid, Horny Goat Weed (*Epimedium grandfiflorum*), Korean *ginseng* (*Panax ginseng*), and saw palmetto berry extract as set forth above and also includes one or more of magnesium aspartate in an amount of about 5 mg to about 35 mg, zinc oxide in an amount of about 3 mg to about 20 mg, and Maca root (*Lepidium meyenii*) in an amount of about 50 mg to about 300 mg.

In some embodiments of the present disclosure, the tablet or capsule of the XL-1 composition includes at least Muira Puama extract, Quercetin, *Chlorophytum borivilianum* (Safed Musli), Dimethylethanolamine (DMAE or DMEA), Vitamin B3 (niacin), *Tribulus terrestris* extract, alpha-lipoic acid, Horny Goat Weed (*Epimedium grandfiflorum*), Korean ginseng (*Panax ginseng*), saw palmetto berry extract, magnesium aspartate, zinc oxide, and Maca root (*Lepidium meyenii*) as set forth above and also includes one or more of: *Avena sativa* extract (oat straw) in an amount of about 20 mg to about 120 mg, amino acid L-Taurine in an amount of about 4 mg to about 25 mg, amino acid L-Lysine in an amount of about 4 mg to about 25 mg, amino acid L-Arginine in an amount of about 4 mg to about 25 mg, and/or amino acid L-Carnitine in an amount of about 4 mg to about 25 mg.

In some embodiments of the present disclosure, the tablet or capsule of the XL-1 composition includes the components in any combination and amount as disclosed herein so long as the ratio of each component is as shown as the amount (mg) per capsule (AMT/CAPSULE (mg)) in Table 1. For example, the XL-1 composition may have any amount of each component within the corresponding range disclosed herein so long as each component is maintained at a ratio of: the Muira Puama extract at about 22.50 mg with: the Quercetin at about 15 mg, the *Chlorophytum borivilianum* at about 125 mg, the dimethylethanolamine (DMAE or DMEA) at about 25 mg, the Vitamin B3 (niacin) at about 3.75 mg, the *Tribulus terrestris* Extract at about 25 mg, the alpha-lipoic acid at about 75 mg, the Horny Goat Weed (*Epimedium grandfiflorum*) at about 62.50 mg, the Korean ginseng (*Panax ginseng*) at about 25 mg, the saw palmetto berry extract at about 15 mg, the magnesium aspartate at about 7.50 mg, the Zinc oxide at about 3.5 mg, the Maca root (*Lepidium meyenii*) at about 62.50 mg, the *Avena sativa* extract at about 25 mg, amino acid L-Taurine at about 5 mg, amino acid L-Lysine at about 5 mg, amino acid L-Arginine at about 5 mg, and amino acid L-Carnitine at about 5 mg.

In some embodiments of the present disclosure, the tablet or capsule of the XL-1 composition has a component ratio disclosed for one capsule in Table 1 and includes Muira Puama extract in an amount of about 22.50 mg up to about 90 mg, Quercetin in an amount of about 15 mg up to about 60 mg, *Chlorophytum borivilianum* in an amount of about 125 mg up to about 500 mg, dimethylethanolamine (DMAE or DMEA) in an amount of about 25 mg up to about 100 mg, Vitamin B3 (niacin) in an amount of about 3.75 mg up to about 15 mg, *Tribulus terrestris* Extract in an amount of about 25 mg up to about 100 mg, alpha-lipoic acid in an amount of about 75 mg up to about 300 mg, Horny Goat Weed (*Epimedium grandfiflorum*) in an amount of about 62.50 mg up to about 250 mg, Korean ginseng (*Panax ginseng*) in an amount of about 25 mg up to about 100 mg, and saw palmetto berry extract in an amount of about 15 mg up to about 60 mg.

In some embodiments of the present disclosure, the tablet or capsule of the XL-1 composition has a component ratio disclosed for one capsule in Table 1 and includes at least Muira Puama extract, Quercetin, *Chlorophytum borivilianum* (Safed Musli), Dimethylethanolamine (DMAE or DMEA), Vitamin B3 (niacin), *Tribulus terrestris* Extract, alpha-lipoic acid, Horny Goat Weed (*Epimedium grandfiflorum*), *Panax ginseng* (Korean *ginseng*), and saw palmetto berry extract as set forth above and also includes one or more of magnesium aspartate in an amount of about 7.50 mg to about 30 mg, Zinc oxide in an amount of about 3.75 mg to about 15 mg, and Maca root (*Lepidium meyenii*) in an amount of about 62.50 mg to about 250 mg.

In some embodiments of the present disclosure, the tablet or capsule of the XL-1 composition has a component ratio disclosed for one capsule in Table 1 and includes Muira Puama extract, Quercetin, *Chlorophytum borivilianum* (Safed Musli), Dimethylethanolamine (DMAE or DMEA), Vitamin B3 (niacin), *Tribulus terrestris* extract, alpha-lipoic acid, Horny Goat Weed (*Epimedium grandfiflorum*), Korean ginseng (*Panax ginseng*), saw palmetto berry extract, magnesium aspartate, Zinc oxide, and Maca root (*Lepidium meyenii*) as set forth above and also includes one or more of: *Avena sativa* extract (oat straw) in an amount of about 25 mg to about 100 mg, amino acid L-Taurine in an amount of about 5 mg to about 20 mg, amino acid L-Lysine HCl in an amount of about 5 mg to about 20 mg, amino acid L-Arginine in an amount of about 5 mg to about 25 mg, and/or an amino acid L-Carnitine in an amount of about 5 mg to about 20 mg.

TABLE 1

| | ACTIVE INGREDIENTS | PRODUCT TYPE | DAILY SERVING (mg) | AMT/ CAPSULE (mg) |
|---|---|---|---|---|
| 1 | Muira Puama extract | Ratio Extract | 90.00 | 22.50 |
| 2 | Quercetin | Chemical/Vitamin | 60.00 | 15.00 |
| 3 | *Chlorophytum Borivilianum* (Safed Musli) | Standardized Extract | 500.00 | 125.00 |
| 4 | Dimethylethanolamine (DMAE) | Ratio Extract | 100.00 | 25.00 |
| 5 | Vitamin B3 (Niacin) | Chemical/Vitamin | 15.00 | 3.75 |
| 6 | *Tribulus Terrestris* Extract | Standardized Extract | 100.00 | 25.00 |
| 7 | Alpha lipoic acid | Chemical | 300.00 | 75.00 |
| 8 | Horny goat weed (*Epimedium*) | Standardized Extract | 250.00 | 62.50 |
| 9 | *Panax Ginseng* | Standardized Extract | 100.00 | 25.00 |
| 10 | saw palmetto berry | Powder | 60.00 | 15.00 |
| 11 | Magnesium (as magnesium aspartate) | Mineral | 30.00 | 7.50 |
| 12 | Zinc (Zinc Oxide) | Mineral | 15.00 | 3.75 |
| 13 | Maca root | Standardized Extract | 250.00 | 62.50 |
| 14 | *Avena Sativa* extract (Oat Straw) | Standardized Extract | 100.00 | 25.00 |
| 15 | L-Arginine | Chemical/Vitamin | 20 | 5.00 |
| 16 | L-Carnitine | Chemical/Vitamin | 20 | 5.00 |
| 17 | L-Lysine | Chemical/Vitamin | 20 | 5.00 |
| 18 | L-Taurine | Chemical/Vitamin | 20 | 5.00 |
| | TOTAL INGREDIENTS | | 2050 | 512.50 |

In some embodiments of the present disclosure, a method for improving erectile function or decreasing erectile dysfunction includes a male subject suffering from erectile dysfunction or needing improved erectile function taking (e.g., oral administration) a dose of one of the XL-1 compositions having one of the disclosed combinations of components (e.g., active ingredients). For treatment, the dosing of the XL-1 composition may be in a solid or liquid formulation that may be taken orally from once per day up to four times per day depending on the concentration of the components in each tablet/capsule and/or the formulation of each tablet/capsule. As would be understood by those of ordinary skill in the art, an XL-1 oral composition may be made of any amount as disclosed herein of any combination as disclosed so long as the amount of each component is within the corresponding range disclosed for each component and the ratio of each component is maintained as set forth herein. As also understood by one of ordinary skill in the art, the weight and metabolism for each male subject consuming the XL-1 oral composition may vary and therefore, taking a lower dose of the composition may allow for determining the specific effects and reactions for an individual male subject to reach an effective dose. Additionally, once an effective amount and/or tolerance is determined for a male subject, it may be possible to either increase the number of oral compositions (e.g., solid or liquid formulations) consumed per day, or alternatively, the concentration of the oral composition may be increased thereby requiring taking fewer pills or liquid doses per day.

In some embodiments, the XL-1 composition may be one oral composition made of the minimal amount of each component up to the base ratio amount (amount for 1 capsule in Table 1) of each component as set forth in any one of the combinations of components as disclosed herein, and the one oral composition may be taken orally up to 4 times per day. In another example, the XL-1 composition may be one oral composition made of about one-third the maximum amount disclosed for each component as set forth in any one of the combinations of components as disclosed herein, and this oral composition may be taken up to 3 times per day. In another example the XL-1 composition may be one oral composition made of about twice the minimal amount (or about half the maximum amount) disclosed for each component as set forth in any one of the combinations of components as disclosed herein, and this oral composition may be taken up 2 times per day. In another example the XL-1 composition may be one oral composition made of the maximum amount disclosed for each component or the total daily serving in Table 1 in any one of the combinations of components as disclosed herein, and this tablet/capsule may be taken once per day. Additionally, oral composition made of more than the base ratio amount may be made in an extended release formulation in order to release the higher concentration of components over time.

The following examples are presented for illustrative purposes only, and do not limit the scope or content of the present application.

EXAMPLES

Example 1

Figure 2A:
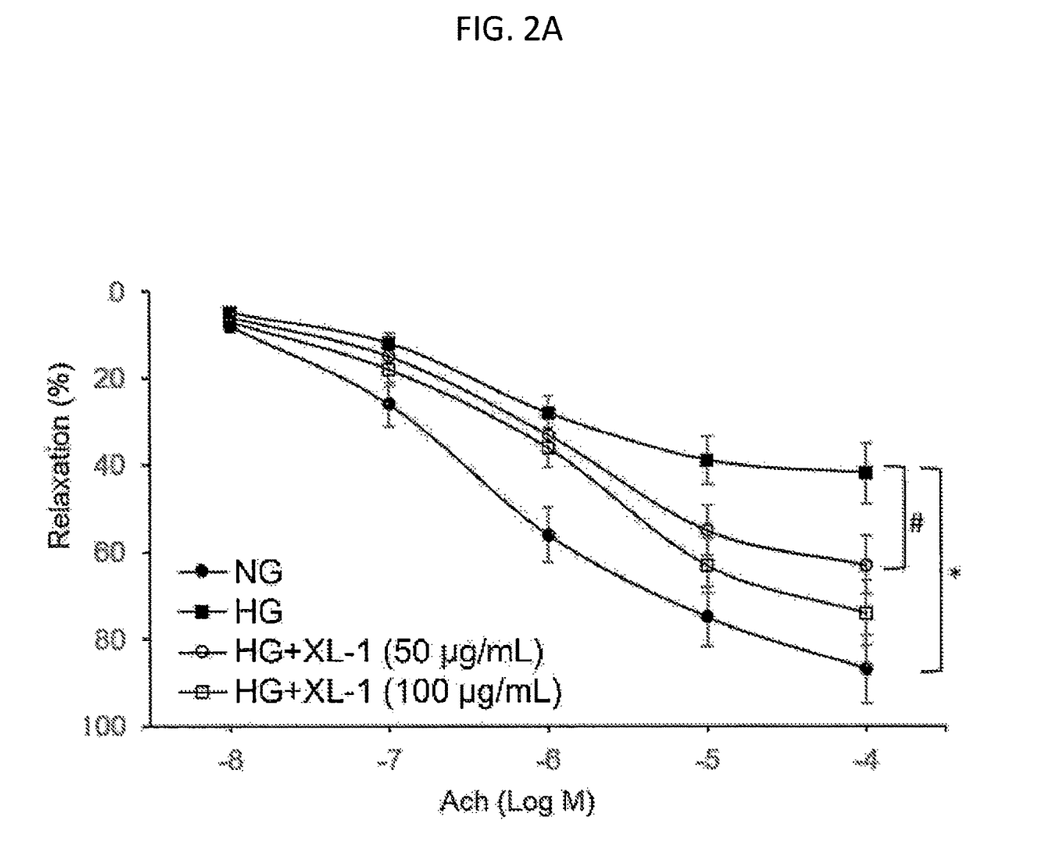
FIG. 2A is a graph showing the percentage of acetylcholine (Ach)-induced relaxation (i.e., endothelium-dependent vasodilation) in aortic rings harvested from normoglycemia (NG) mice or hyperglycemia (HG) mice, in which the percentage of relaxation in aortic rings from NG mice and incubated with Ach alone is shown in black circles, aortic rings from hyperglycemia (HG) mice and incubated with Ach alone is shown in black squares, aortic rings from HG mice and incubated with Ach and 50 µg/mL XL-1 is shown in open circles, and aortic rings from HG mice and incubated with Ach and 100 µg/mL XL-1 is shown in open squares, according to embodiments of the present disclosure.

XL-1 reverses hyperglycemia-induced endothelial dysfunction. Diabetes is an established risk factor for sexual dysfunction in men, as a threefold increased risk of erectile dysfunction was documented in diabetic men, as compared with nondiabetic men. The XL-1 (XtraLast) alleviated hyperglycemia-induced endothelial dysfunction in vivo. Hyperglycemia was induced in mice by STZ injection, and aortas were harvested and cut into 3-mm sections. Ring segments were incubated ex vivo with XL-1 50 μg/mL or 100 μg/mL overnight in endothelial cell basal medium at 37° C. The aortic rings were subjected to a vasomotor reactivity assay i.e. endothelium-dependent (acetylcholine-induced relaxation) and -independent vasodilation (sodium nitroprusside-induced relaxation). With reference to FIG. 2A, hyperglycemia compromised acetylcholine-induced endothelium-dependent relaxation. Additionally, treatment of XL-1 significantly restored hyperglycemia-impaired endothelium-dependent relaxation. In contrast, NO donor-triggered endothelium-independent relaxation was not altered by the presence of different treatment factors (FIG. 2B).

Figure 2B:
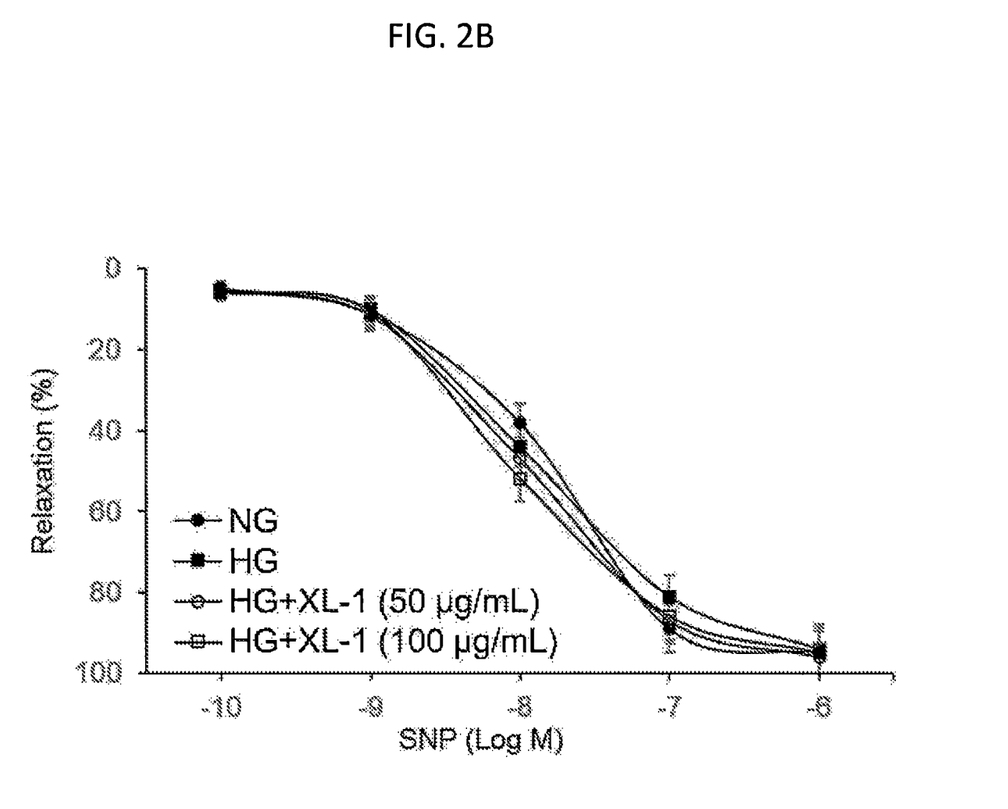
FIG. 2B is a graph showing the percentage of sodium nitroprusside (SNP)-induced relaxation (i.e., endothelium-independent vasodilation) in aortic rings harvested from normoglycemia (NG) mice or hyperglycemia (HG) mice, in which the percentage of relaxation in aortic rings from NG mice and incubated with SNP alone is shown in black circles, aortic rings from hyperglycemia (HG) mice and incubated with SNP alone is shown in black squares, aortic rings from HG mice and incubated with SNP and 50 µg/mL XL-1 is shown in open circles, and aortic rings from HG mice and incubated with SNP and 100 µg/mL XL-1 is shown in open squares, according to embodiments of the present disclosure.

With reference to FIG. 2B, nitric oxide (NO) donor-triggered endothelium-independent relaxation was not altered by the presence of different treatment factors. For this experiment, C57BL/6J mice were divided into four groups (6 mice/group) and injected with vehicle or streptozotocin (STZ) to induce hyperglycemia. Aortas were all harvested three weeks after STZ administration and cut into 3-mm sections. In some experiments, ring segments were incubated ex vivo with 50 μg/mL or 100 μg/mL XL-1 overnight. The aortic rings were subjected to an organ chamber assay of endothelium-dependent and -independent vasodilation. For the data shown in FIGS. 2A-2B, N=6, *P<0.01 vs NG; #P<0.01 vs HG. NG indicates normoglycemia; HG, hyperglycemia; Ach, acetylcholine; SNP, sodium nitroprusside.

Example 2

Figure 3A:
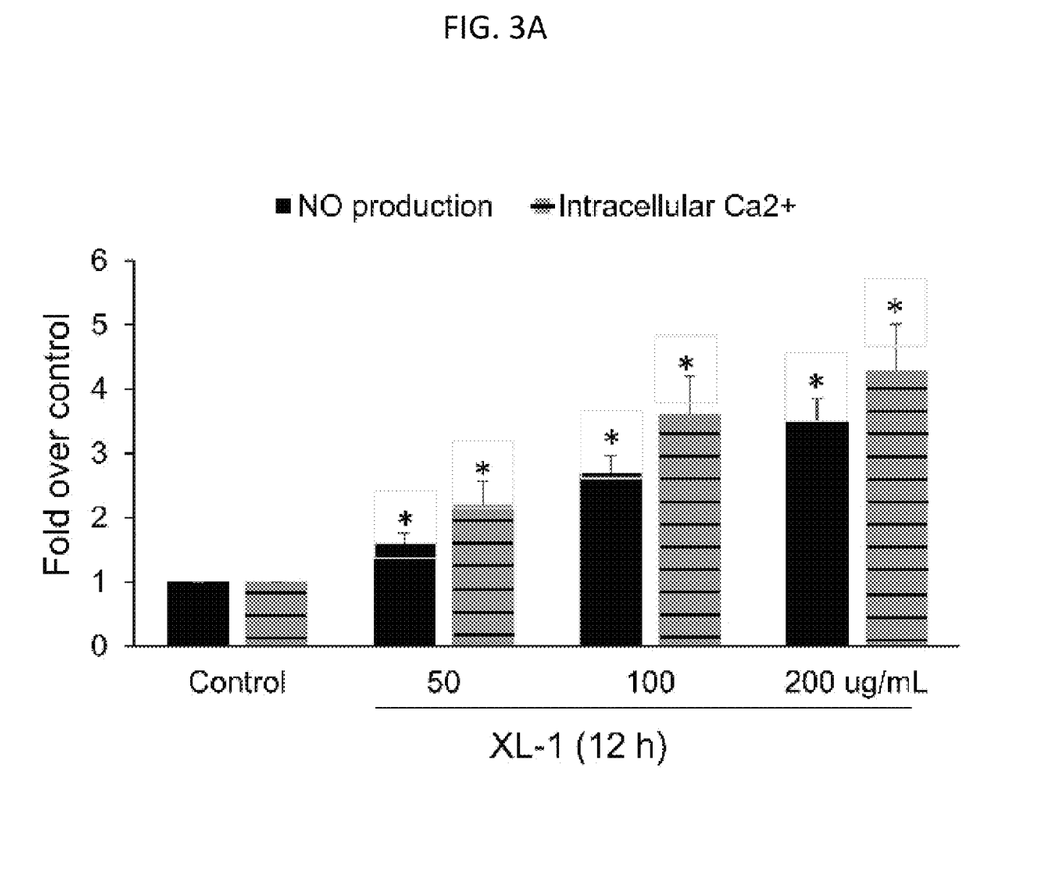
FIG. 3A is a graph showing the amount of nitric oxide (NO) (solid black bars) and intracellular calcium ($Ca^{2+}$) (striped bars) in bovine aortic endothelial cells (BAECs) incubated for 12 hours in culture media alone (control) or with 50, 100, or 200 µg/mL XL-1 as indicated, according to embodiments of the present disclosure.
Figure 3B:
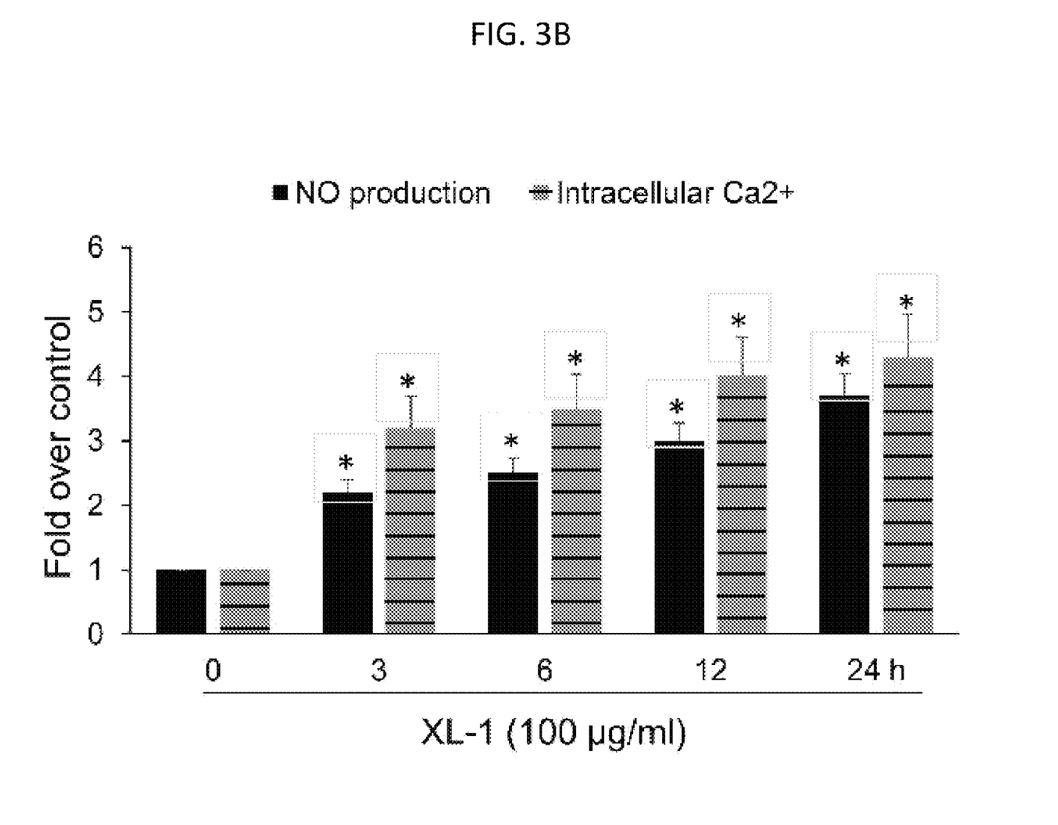
FIG. 3B is a graph showing the amount of nitric oxide (NO) (solid black bars) and intracellular calcium ($Ca^{2+}$) (striped bars) in bovine aortic endothelial cells (BAECs) incubated with 100 ug/mL of XL-1 for 0, 3, 6, 12, or 24 hours as indicated, according to embodiments of the present disclosure.

With reference to FIGS. 3A-3B, the XL-1 composition nitric oxide (NO) release from endothelial cells and intracellular calcium. In particular, incubation of bovine aortic endothelial cells (BAEC) with the XL-1 composition resulted in a time- and dose-dependent NO release as well as an increase in intracellular calcium. Maximum NO release was measured 24 hour after addition of XL-1. As is well known in the art, NO is essential for endothelial function, and reduced NO bioactivity is involved in the pathogenesis of many cardiovascular disorders such as hypertension, atherosclerosis, venous bypass graft disease, diabetic vascular disease. The XL-1 composition increases NO release from endothelial cells, thereby inducing vessel relaxation which is known to increase cardiovascular function.

Bovine aortic endothelial cells (BAEC) and cell culture media were obtained from Clonetics Inc. (Walkersville, Md.). BAEC were grown in EBM supplemented with 2% fetal bovine serum (FBS). Confluent monolayers of BAEC were treated with various doses of XL-1 (50, 10, or 200 ug/mL) for 12 hours (h) (FIG. 3A) or with 100 ug/mL XL-1 for various times (0, 3, 6, 12, or 24 h) (FIG. 3B). Control cells were treated with vehicle only. After treatment, NO released by BAEC was measured as nitrite (a stable metabolite of NO) concentration in cell culture supernatants as described in Cho et al., 2004, JBC, 279:2499-2506, the entire content of which is incorporated herein by reference.

The XL-1 composition of the present disclosure shows effects on intracellular calcium ([Ca2+]i) as measured using a fluorescence technique. Cell proteins were separated on a sodium dodecyl sulfate—(SDS)-polyacrylamide gel and electrophoretically transferred onto nitrocellulose membranes. Each bar represents mean NO production and ([Ca2+]I (after normalization to total cellular protein) as fold increases above control ±S. D. Statistically significant at *p<0.05 vs. control.

Example 3

Case 1. Mr. Li, 40 years old was capable of an erection without erectile rigidness, and he experienced premature ejaculation and weak sexual intercourse. After taking 4 capsules of the XL composition orally each day for 1 week, Mr. Li experienced significantly enhanced erectile rigidness (e.g., hardness), the length of the penis was increased, and premature ejaculation decreased or did not occur.

Case 2. Mr. Yu, 42 years old, experienced high levels of stress, had no desire for sexual intercourse, and experienced premature ejaculation. After taking 4 capsules of the XL composition orally each day for 1 week, Mr. Li experienced increased physical activity, improved sensitivity to sexual stimulation, a decrease in the time to erection, and extended sexual intercourse up to 30 minutes. Mr. Yu also experienced notable increase in size of erect penis thereby increasing desire for intercourse and increased happiness.

Case 3. Mr. Lee, a 45-year-old businessman, was using prescription drugs (e.g., Viagra) for erectile dysfunction. While the prescription drugs facilitated erection, the erection did not correspond with an emotional desire for intercourse. After taking 4 capsules of the XL composition orally each day for 1 week, Mr. Lee experienced a natural stimulation and arousal. Mr. Lee experienced increased control with erections where the erections occurred more naturally when he desired to have sex, and he was able to become erect more than once.

As used herein, unless otherwise expressly specified, all numbers such as those expressing values, ranges, amounts or percentages may be read as if prefaced by the word "about", even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition for improving erectile function or treating erectile dysfunction, the composition made of active ingredients comprising:

Muira Puama extract, Quercetin, *Chlorophytum borivilianum* (Safed Musli), Dimethylethanolamine (DMAE), niacin (Vitamin B3), *Tribulus terrestris* extract, alpha-lipoic acid, Horny Goat Weed (*Epimedium grandfiflorum*), Korean *ginseng* (*Panax ginseng*), and saw palmetto berry extract.

2. The composition of claim 1, further comprising magnesium aspartate, Zinc oxide, and/or Maca root (*Lepidium meyenii*).

3. The composition of claim 2, wherein the Muira Puama extract is in an amount of about 15 mg to about 100 milligrams (mg), the Quercetin is in an amount of about 10 mg to about 75 mg, *Chlorophytum borivilianum* is in an amount of about 100 mg to about 600 mg, DMAE is in an amount of about 20 mg to about 120 mg, niacin is in an amount of about 3 mg to about 20 mg, *Tribulus terrestris* extract is in an amount of about 20 mg to about 120 mg, alpha-lipoic acid is in an amount of about 60 mg to about 400 mg, Horny Goat Weed (*Epimedium grandfiflorum*) is in an amount of about 50 mg to about 300 mg, *Panax ginseng* is in an amount of about 20 mg to about 120 mg, saw palmetto berry extract is in an amount of about 10 mg to about 75 mg, magnesium aspartate is in an amount of about 5 mg to about 35 mg, Zinc oxide is in an amount of about 3 mg to about 20 mg, and Maca root (*Lepidium meyenii*) is in an amount of about 50 mg to about 300 mg.

4. The composition of claim 2, wherein the composition further comprises one or more of *Avena sativa* extract (oat straw), L-Taurine, L-Lysine, L-Arginine, and/or L-Carnitine.

5. The composition of claim 4, wherein the *Avena sativa* extract (oat straw) is in an amount of about 20 mg to about 120 mg, the L-Taurine is in an amount of about 4 mg to about 25 mg, the L-Lysine is in an amount of about 4 mg to about 25 mg, the L-Arginine is in an amount of about 4 mg to about 25 mg, and/or the L-Carnitine is in an amount of about 4 mg to about 25 mg.

6. The composition of claim 1, wherein the Muira Puama extract is in an amount of about 22.50 mg, the Quercetin is in an amount of about 15 mg, the *Chlorophytum borivilianum* is in an amount of about 125 mg, the DMAE is in an amount of about 25 mg, the niacin is in an amount of about 3.75 mg, the *Tribulus terrestris* Extract is in an amount of about 25 mg, the alpha-lipoid acid is in an amount of about 75 mg, the Horny Goat Weed (*Epimedium grandfiflorum*) is in an amount of about 62.50 mg, the Korean *ginseng* (*Panax ginseng*) is in an amount of about 25 mg, and the saw palmetto berry extract is in an amount of about 15 mg.

7. The composition of claim 2, wherein the Muira Puama extract is in an amount of about 22.50 mg, the Quercetin is in an amount of about 15 mg, the *Chlorophytum borivilianum* is in an amount of about 125 mg, the DMAE is in an amount of about 25 mg, the niacin is in an amount of about 3.75 mg, the *Tribulus terrestris* Extract is in an amount of about 25 mg, the alpha-lipoid acid is in an amount of about 75 mg, the Horny Goat Weed (*Epimedium grandfiflorum*) is in an amount of about 62.50 mg, the *Panax ginseng* is in an amount of about 25 mg, the saw palmetto berry extract is in an amount of about 15 mg, the magnesium aspartate is in an amount of about 7.50 mg, the Zinc oxide is in an amount of about 3.5 mg, and the Maca root (*Lepidium meyenii*) is in an amount of about 62.50 mg.

8. The composition of claim 5, wherein the Muira Puama extract is in an amount of about 22.50 mg, the Quercetin is in an amount of about 15 mg, the *Chlorophytum borivilianum* is in an amount of about 125 mg, the DMAE is in an amount of about 25 mg, the niacin is in an amount of about 3.75 mg, the *Tribulus terrestris* Extract is in an amount of about 25 mg, the alpha-lipoid acid is in an amount of about 75 mg, the Horny Goat Weed (*Epimedium grandfiflorum*) is in an amount of about 62.50 mg, the *Panax ginseng* is in an amount of about 25 mg, the saw palmetto berry extract is in an amount of about 15 mg, the magnesium aspartate is in an amount of about 7.50 mg, the Zinc oxide is in an amount of about 3.5 mg, the Maca root (*Lepidium meyenii*) is in an amount of about 62.50 mg, the *Avena sativa* extract is in an amount of about 25 mg, the L-Taurine is in an amount of about 5 mg, the L-Lysine is in an amount of about 5 mg, the L-Arginine is in an amount of about 5 mg, and the L-Carnitine is in an amount of about 5 mg.

9. The composition of claim 8, wherein the L-Lysine is L-Lysine HCl.

10. The composition of claim 4, wherein the Muira Puama extract is in an amount of about 22.50 mg, the Quercetin is in an amount of about 15 mg, the *Chlorophytum borivilianum* is in an amount of about 125 mg, the DMAE is in an amount of about 25 mg, the niacin is in an amount of about 75 mg, the Horny Goat Weed (*Epimedium grandfiflorum*) is in an amount of about 62.50 mg, the *Panax ginseng* is in an amount of about 25 mg, the saw palmetto berry extract is in an amount of about 15 mg, the magnesium aspartate is in an amount of about 7.50 mg, the Zinc oxide is in an amount of about 3.5 mg, the Maca root (*Lepidium meyenii*) is in an amount of about 62.50 mg, the *Avena sativa* extract is in an amount of about 25 mg, the L-Taurine is in an amount of about 5 mg, the L-Lysine is in an amount of about 5 mg, the L-Arginine is in an amount of about 5 mg, and the L-Carnitine is in an amount of about 5 mg.

11. The composition of claim 10, wherein the composition is a solid oral composition or a liquid oral composition.

12. The composition of claim 11, wherein the solid oral composition is a tablet or a capsule.

13. The composition of claim 1, further comprising an excipient.

14. The composition of claim 13, wherein the excipient is selected from cellulose, rice flour, magnesium stearate, gelatin, and/or Food, Drugs, and Cosmetics (FD&C) Blue No. 1.

15. A method for improving erectile function or decreasing erectile dysfunction in a male subject, the method comprising administering the composition of claim 1 to the male subject.

16. A method for improving erectile function or decreasing erectile dysfunction in a male subject, the method comprising administering the composition of claim 2 to the male subject.

17. A method for improving erectile function or decreasing erectile dysfunction in a male subject, the method comprising administering the composition of claim 3 to the male subject.

18. A method for improving erectile function or decreasing erectile dysfunction in a male subject, the method comprising administering the composition of claim 5 to the male subject.

19. A method for improving erectile function or decreasing erectile dysfunction in a male subject, the method comprising administering the composition of claim 10 to the male subject.

20. The method of claim 19, wherein the composition is an oral composition in tablet or capsule form and the administering comprises taking 4 tablets or capsules per day.

* * * * *

UNITED STATES PATENT AND TRADEMARK OFFICE
CERTIFICATE OF CORRECTION

| | |
|---|---|
| PATENT NO. | : 11,135,259 B2 |
| APPLICATION NO. | : 16/239475 |
| DATED | : October 5, 2021 |
| INVENTOR(S) | : Yong Wu et al. |

It is certified that error appears in the above-identified patent and that said Letters Patent is hereby corrected as shown below:

In the Claims

Column 12, Line 18, Claim 6    delete "alpha-lipoid" and insert -- alpha-lipoic --

Column 12, Line 29, Claim 7    delete "alpha-lipoid" and insert -- alpha-lipoic --

Column 12, Line 43, Claim 8    delete "alpha-lipoid" and insert -- alpha-lipoic --

Signed and Sealed this
Eighth Day of November, 2022

Katherine Kelly Vidal
*Director of the United States Patent and Trademark Office*